(12) United States Patent
Murooka et al.

(10) Patent No.: US 8,164,751 B2
(45) Date of Patent: Apr. 24, 2012

(54) OPTICAL SYSTEM, METHOD, AND COMPUTER READABLE MEDIUM FOR DETERMINING THICKNESS OF A MEDIUM

(75) Inventors: Takashi Murooka, Ashigarakami-gun (JP); Hideyasu Ishibashi, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 426 days.

(21) Appl. No.: 12/415,284

(22) Filed: Mar. 31, 2009

(65) Prior Publication Data
US 2009/0244537 A1   Oct. 1, 2009

(30) Foreign Application Priority Data
Mar. 31, 2008   (JP) .................................. 2008-093397

(51) Int. Cl.
*G01J 4/00* (2006.01)
*G01N 21/00* (2006.01)
(52) U.S. Cl. .................... 356/364; 356/337; 356/630
(58) Field of Classification Search .......... 356/364–370, 356/625, 630
See application file for complete search history.

(56) References Cited

U.S. PATENT DOCUMENTS
4,672,196 A * 6/1987 Canino .................. 250/225
6,624,890 B2 * 9/2003 Backman et al. ........... 356/369

FOREIGN PATENT DOCUMENTS
WO   96/28721 A1   9/1996

* cited by examiner

*Primary Examiner* — Tarifur Chowdhury
*Assistant Examiner* — Tara S Pajoohi
(74) *Attorney, Agent, or Firm* — Sughrue Mion, PLLC

(57) ABSTRACT

An optical system includes a light sending section that sends light to an object having a scattering medium and a lower medium positioned below the scattering medium, where the scattering medium scatters light and the lower medium feeds back polarized light in response to light incident thereon, a light receiving section that receives (i) light that is sent from the light sending section and then scattered by the scattering medium and (ii) light from the lower medium, and a thickness calculating section that calculates a thickness of the scattering medium, by referring to at least one of a non-polarization component and a polarization component of the light received by the light receiving section.

18 Claims, 11 Drawing Sheets

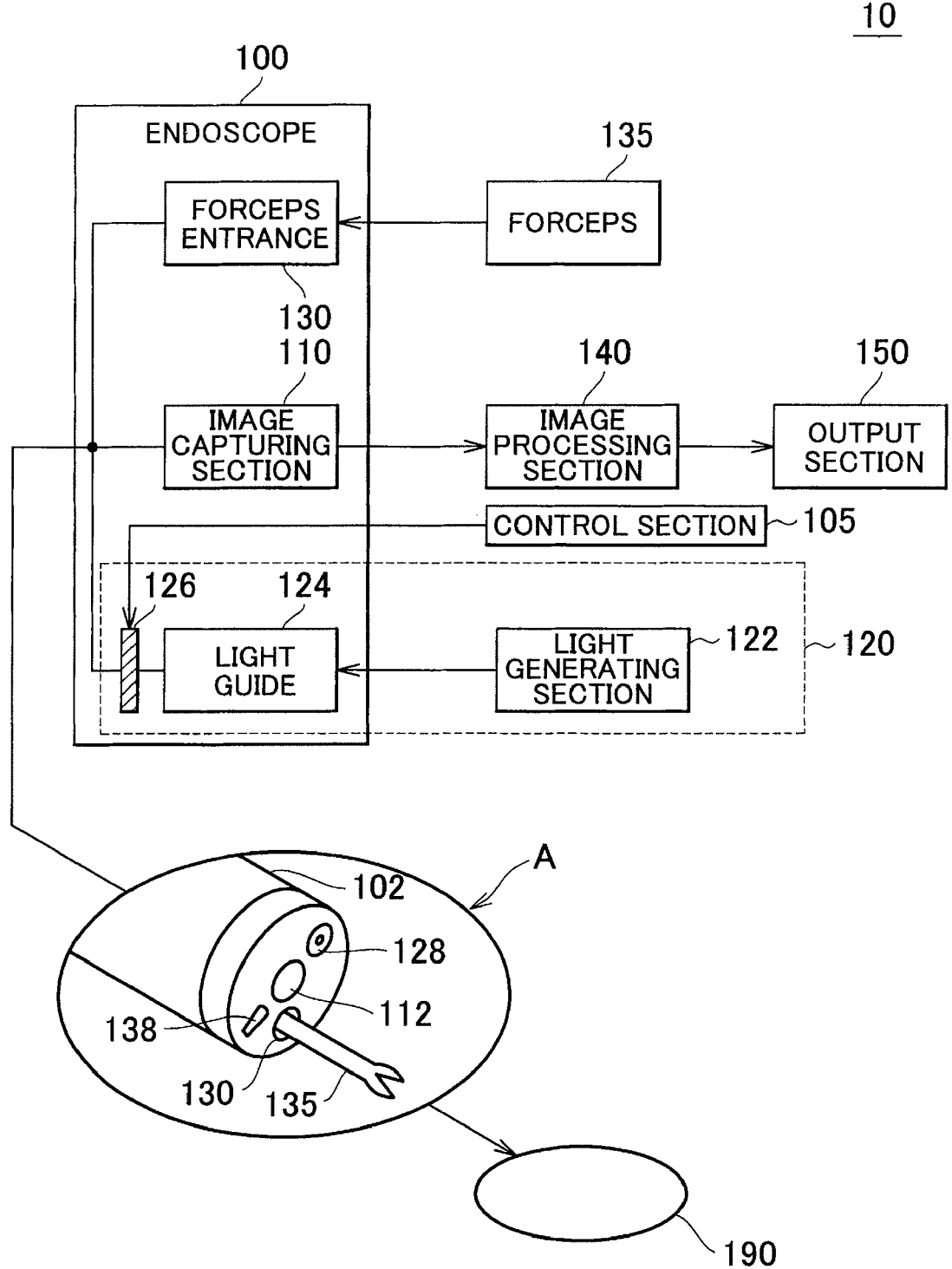
F I G. 1

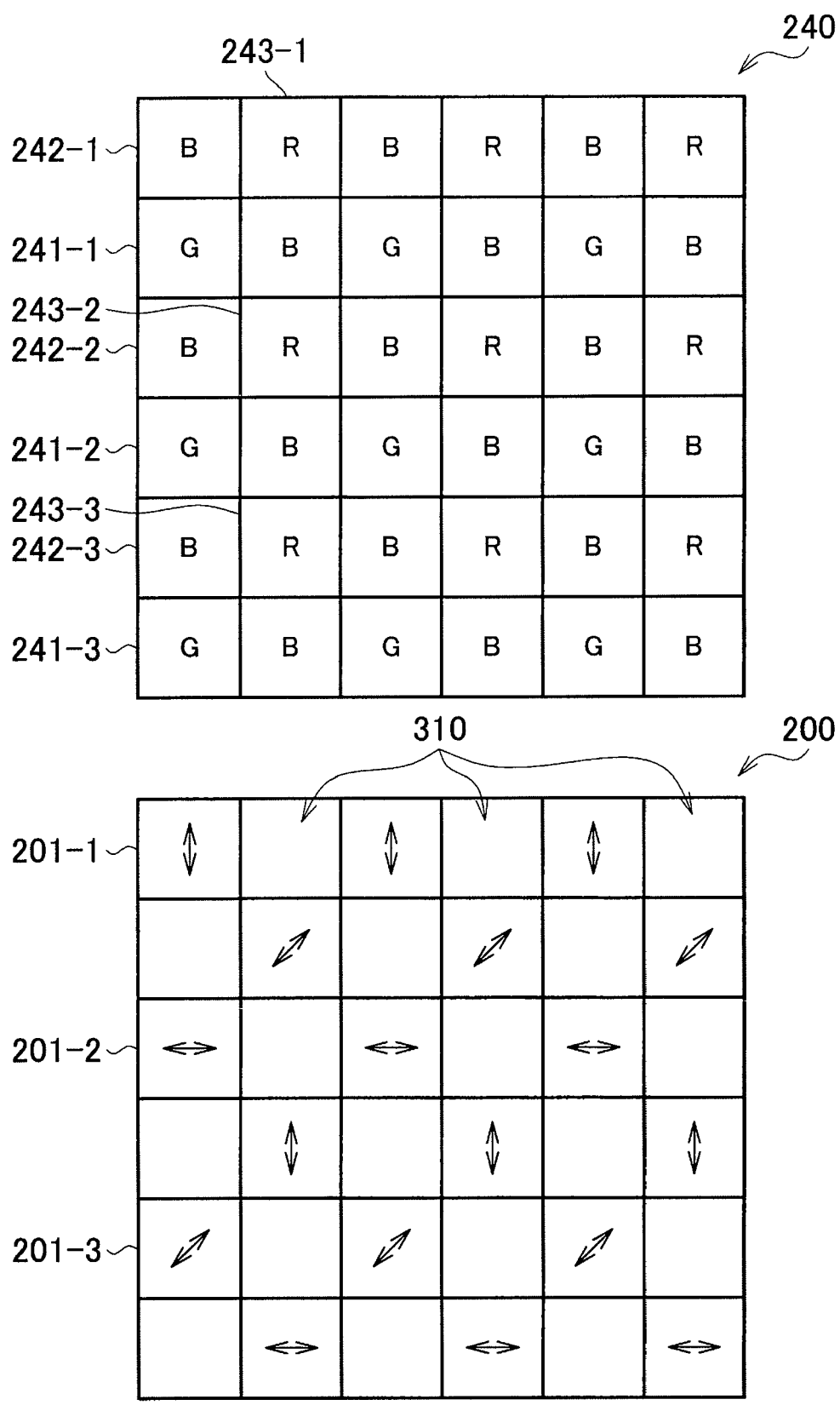
F I G. 3

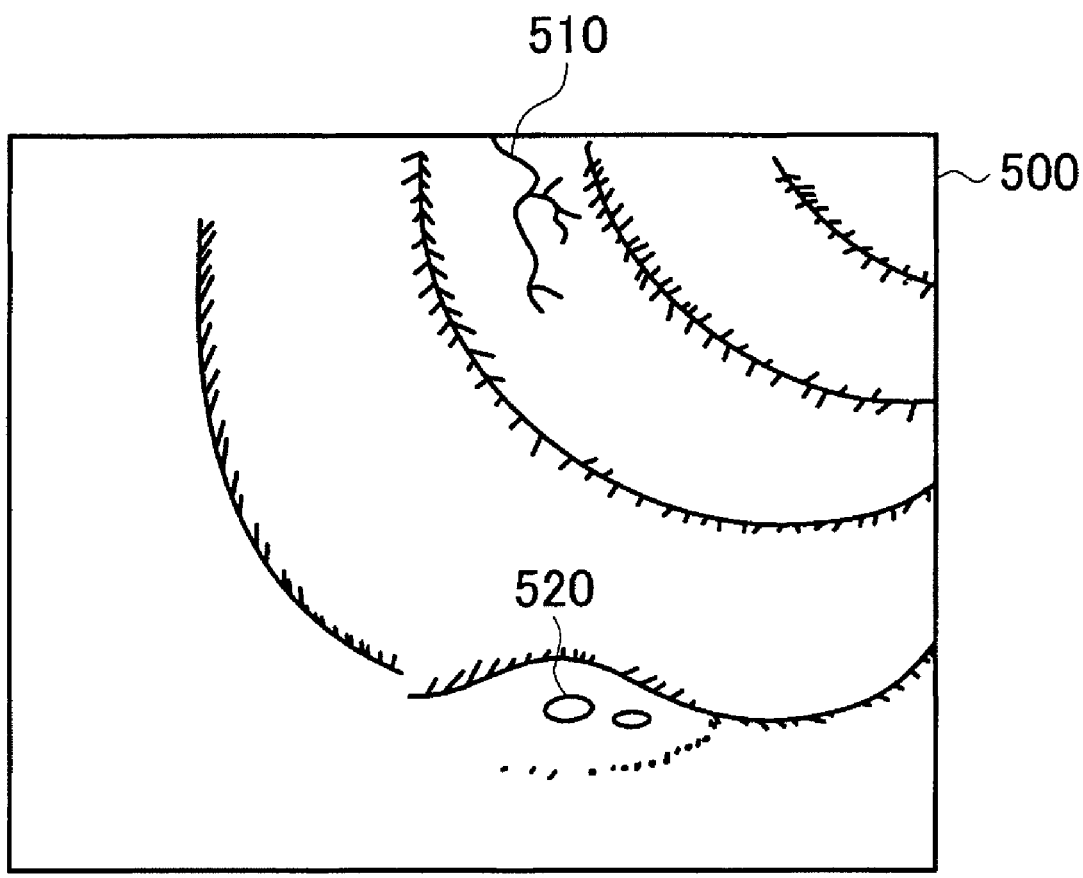
F I G . 5

| DEGREE OF POLARIZATION | THICKNESS |
|---|---|
| P1 | D1 |
| P2 | D2 |
| ⋮ | ⋮ |

FIG. 9

OPTICAL SYSTEM, METHOD, AND COMPUTER READABLE MEDIUM FOR DETERMINING THICKNESS OF A MEDIUM

CROSS REFERENCE TO RELATED APPLICATION

The present application claims priority from a Japanese Patent Application No. 2008-93397 filed on Mar. 31, 2008, the contents of which are incorporated herein by reference.

BACKGROUND

1. Technical Field

The present invention relates to an optical system, a method and a computer readable medium. More particularly, the present invention relates to an optical system for optically calculating the thickness of a scattering medium, a method for optically calculating the thickness of a scattering medium, and a computer readable medium storing a program for use with the optical system.

2. Related Art

A known examination apparatus is used for detecting foreign substances attached to silicon crystal surfaces and/or amorphous silicon thin film surfaces, for measuring crystal defects such as oxygen precipitate formation within silicon wafers, and for measuring foreign substances within amorphous silicon thin films as disclosed, for example, in International Publication No. WO 96/028721.

The technique disclosed in the above publication, however, is incapable of calculating the thickness of scattering media.

SUMMARY

Therefore, it is an object of an aspect of the innovations herein to provide an optical system, a method and a compute readable medium, which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary optical system may include a light sending section that sends light to an object having a scattering medium and a lower medium positioned below the scattering medium, where the scattering medium scatters light and the lower medium feeds back polarized light in response to light incident thereon, a light receiving section that receives (i) light that is sent from the light sending section and then scattered by the scattering medium and (ii) light from the lower medium, and a thickness calculating section that calculates a thickness of the scattering medium, by referring to at least one of a non-polarization component and a polarization component of the light received by the light receiving section.

According to the second aspect related to the innovations herein, one exemplary method may include sending light to an object having a scattering medium and a lower medium positioned below the scattering medium, where the scattering medium scatters light and the lower medium feeds back polarized light in response to light incident thereon, receiving (i) light that is sent in the light sending and scattered by the scattering medium and (ii) light from the lower medium, and calculating a thickness of the scattering medium, by referring to at least one of a non-polarization component and a polarization component of the light received in the light receiving.

According to the third aspect related to the innovations herein, one exemplary computer readable medium may store thereon a program for use with an optical system. The program causes a computer to function as a light sending section that sends light to an object having a scattering medium and a lower medium positioned below the scattering medium, where the scattering medium scatters light and the lower medium feeding back polarized light in response to light incident thereon, a light receiving section that receives (i) light that is sent from the light sending section and then scattered by the scattering medium and (ii) light from the lower medium, and a thickness calculating section that calculates a thickness of the scattering medium, by referring to at least one of a non-polarization component and a polarization component of the light received by the light receiving section.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 illustrates an exemplary configuration of an optical system 10 relating to an embodiment of the present invention, together with a living organism 190.

FIG. 3 illustrates exemplary arrangement of light receiving elements in a light receiving section 240 and exemplary arrangement of polarizing elements in a polarization filter 200.

FIG. 5 illustrates an exemplary image 500 produced by an endoscope 100.

FIG. 9 illustrates exemplary thickness information stored on a thickness calculating section 460, by using a table.

DESCRIPTION OF EXEMPLARY EMBODIMENTS

Figure 2:
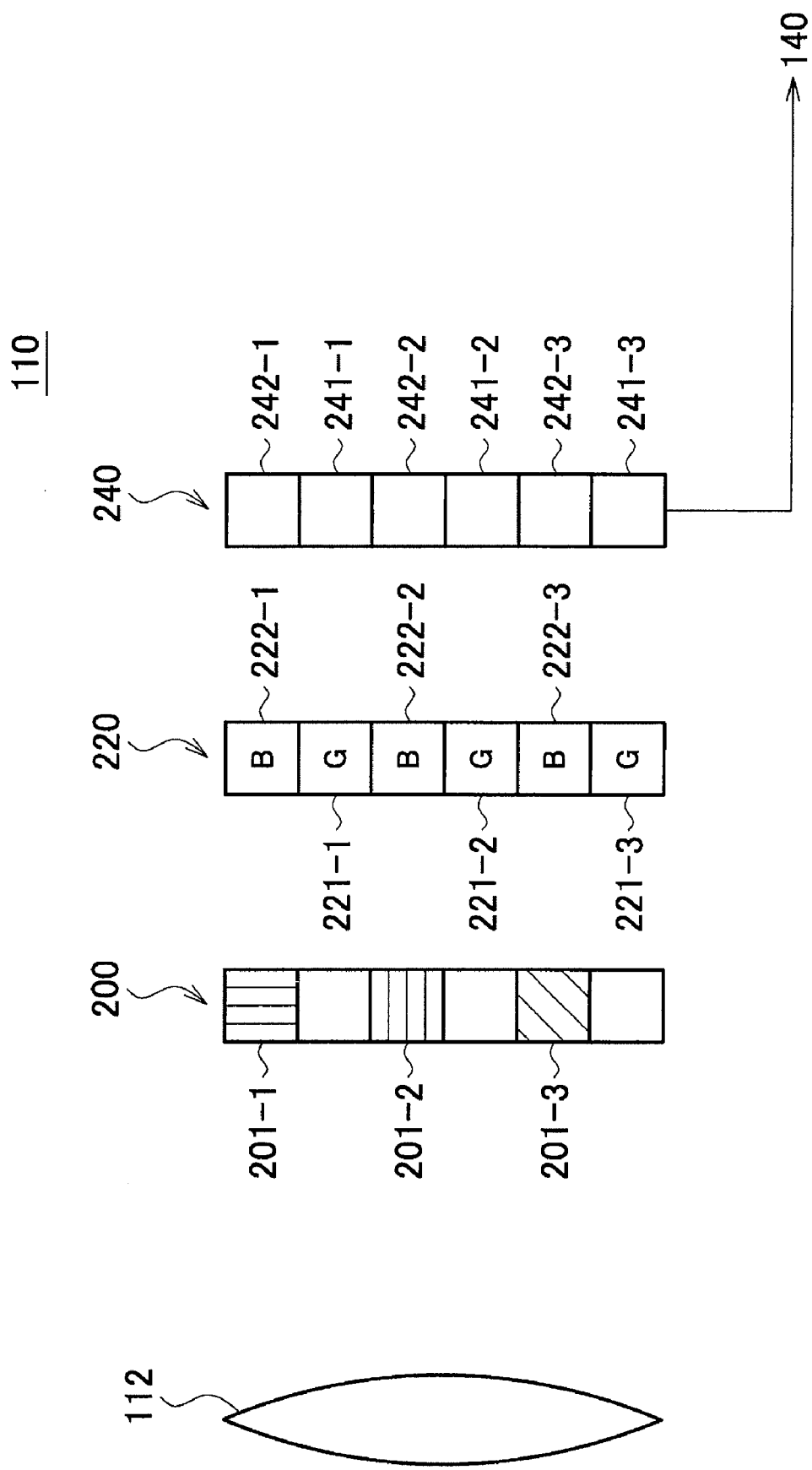
FIG. 2 illustrates an exemplary configuration of an image capturing section 110.

Some aspects of the invention will now be described based on the embodiments, which do not intend to limit the scope of the present invention, but exemplify the invention. All of the features and the combinations thereof described in the embodiment are not necessarily essential to the invention.

FIG. 1 illustrates an exemplary configuration of an optical system 10 relating to an embodiment of the present invention, together with a living organism 190. The optical system 10 includes an endoscope 100 shown as an example of an image capturing apparatus, a forceps 135, an image processing section 140 shown as an example of an image processing apparatus, a control section 105, a light sending section 120, and an output section 150. In FIG. 1, the reference character A indicates an enlargement view of an end portion 102 of the endoscope 100. Note that the optical system 10 can function as an image capturing system or image processing system as will be subsequently described. The living organism 190 may be shown as an example of an object relating to the present invention. The endoscope 100 may have the light sending section 120 built therein.

The endoscope 100 includes an image capturing section 110, a forceps entrance 130, a light guide 124, and a polarization filter 126. Here, the light guide 124 and polarization filter 126 are part of the light sending section 120. The end portion 102 of the endoscope 100 includes a nozzle 138, a lens 112 constituting part of the image capturing section 110, and a light exit 128 constituting part of the light guide 124. The polarization filter 126 and light guide 124 included in the endoscope 100 and a light generating section 122 provided outside the endoscope 100 together function as the light sending section 120.

A forceps 135 is inserted into the forceps entrance 130, so that the forceps entrance 130 guides the forceps 135 through the end portion 102. The forceps 135 may have an end with any of various shapes. In addition to forciples, a variety of treatment tools for treating the living organism 190 may be inserted into the forceps entrance 130. The nozzle 138 sends out water or air.

The light generating section 122 generates irradiation light to be sent from the light exit 128 to the living organism 190. The light generated by the light generating section 122 contains red, green, and blue components, for example.

The light guide 124 is formed by an optical fiber, for example. The light guide 124 is designed to guide the light generated by the light generating section 122 to the light exit 128 formed in the end portion 102 of the endoscope 100. In the vicinity of the light exit 128, the polarization filter 126 is provided to polarize the light generated by the light generating section 122. The light that is generated by the light generating section 122 and has passed through the polarization filter 126 is sent to the living organism 190 through the light exit 128.

The control section 105 can control the polarization filter 126 to be inserted, at a desired timing, into the optical path of the light to be sent to the living organism 190. The polarization filter 126 may be formed as part of a rotation filter, and the control section 105 may control the rotation of the rotation filter.

The image capturing section 110 receives light from the living organism 190 to capture an image of the living organism 190. Specifically speaking, the image capturing section 110 captures the image of the living organism 190 by using the light that is sent through the light exit 128 to the living organism 190 and then reflected by the living organism 190 and the light that is sent through the light exit 128 to the living organism 190 and then scattered or reflected within the living organism 190.

The image processing section 140 processes an image signal produced by the image capturing section 110 to generate various types of images. The image processing section 140 supplies the generated image to the output section 150. The output section 150 outputs the image supplied from the image processing section 140. The output section 150 may display the image supplied from the image processing section 140. The output section 150 may record the images supplied from the image processing section 140 on a recording medium such as a non-volatile memory.

FIG. 2 illustrates an exemplary configuration of the image capturing section 110. The image capturing section 110 includes the lens 112, a polarization filter 200, a color filter 220 and a light receiving section 240. The lens 112 causes light from an object to be imaged onto the light receiving section 240 through the polarization filter 200 and the color filter 220. The polarization filter 200 may be shown as an example of a polarizing section relating to the present invention.

The polarization filter 200 includes a plurality of polarizing elements 201-1 to 201-3 (hereinafter collectively referred to as the polarizing elements 201). The color filter 220 includes first color filter portions 221-1 to 221-3 (hereinafter collectively referred to as the first color filter portions 221) and second color filter portions 222-1 to 222-3 (hereinafter collectively referred to as the second color filter portions 222). The light receiving section 240 includes first light receiving elements 241-1 to 241-3 (hereinafter collectively referred to as the first light receiving elements 241) and second light receiving elements 242-1 to 242-3 (hereinafter collectively referred to as the second light receiving elements 242).

The first color filter portions 221 transmit green light. The second color filter portions 222 transmit blue light.

The polarizing elements 201 each selectively transmit a specified polarization component of the light from the living organism 190 to guide polarized light to the color filter 220. The transmission axes of the polarizing elements 201-1, 201-2 and 201-3 are respectively oriented in different directions from each other.

For example, light that comes from the living organism 190 and has passed through the polarizing elements 201 further passes through the second color filter portions 222 and is then received by the second light receiving elements 242. Thus, the second light receiving elements 242 receive blue light from the living organism 190. As seen from FIG. 2, no polarizing elements are provided between the polarizing element 201-1 and the polarizing element 201-2. Light that has passed through the polarization filter 200 between the polarizing element 201-1 and the polarizing element 201-2 further passes through the first color filter portions 221 and is then received by the first light receiving elements 241. Thus, the first light receiving elements 241 receive green light from the living organism 190.

The light receiving elements, such as first and second light receiving elements 241 and 242, included in the light receiving section 240 each generate a light reception signal according to the amount of the received light. The light reception signals are supplied to the image processing section 140 as image signals to be processed by the image processing section 140.

FIG. 3 illustrates exemplary arrangement of the light receiving elements in the light receiving section 240 and exemplary arrangement of the polarizing elements in the polarization filter 200. In addition to the above-described first and second light receiving elements 241 and 242, the light receiving section 240 includes a plurality of third light receiving elements 243-1 to 243-3 (hereinafter collectively referred to as the third light receiving elements 243) that are designed to receive red light.

In the light receiving section 240, the first light receiving elements 241 are positioned in the regions denoted by G, the second light receiving elements 242 are positioned in the regions denoted by B, and the third light receiving elements 243 are positioned in the regions denoted by R. Thus, the light receiving section 240 is formed in such a manner that the first, second and third light receiving elements 241, 242 and 243 are arranged in a matrix.

As described above, the first light receiving elements 241 are disposed on substantially the same plane and each designed to receive a first-color component of the light from the living organism 190. The second light receiving elements 242 are each designed to receive a second-color component of the light from the object. Here, note that the second light receiving elements 242 are disposed on substantially the same plane, with a higher area density than the first light receiving elements 241. The second light receiving elements 242 are disposed on substantially the same plane with a higher number or area density than the first and third light receiving elements 241 and 243. The first, second, and third light receiving elements 241, 242 and 243 are disposed on substantially the same plane.

In FIG. 3, the transmission axes of the respective polarizing elements 201 of the polarization filter 200 are indicated by arrows. As seen from FIG. 3, the transmission axes of the polarizing elements 201-1, 201-2 and 201-3 are oriented to extend in different directions. Therefore, each of the polarizing elements 201-1, 201-2 and 201-3 selectively transmits light polarized in a different direction. In other words, first, second and third polarization components of light are polarized in different directions from each other.

The polarizing elements 201-1 and 201-2 are oriented so that their transmission axes are substantially orthogonal to each other. Thus, the first and second polarization components of the light are substantially orthogonal to each other. More specifically, the first and second polarization components of the light are polarized in directions substantially orthogonal to each other. When a given polarization component of light is substantially orthogonal to a different polarization component of the light, their polarization states may be represented by two points symmetrical with respect to the origin on the surface of the Poincaré sphere, for example, a pair of linearly polarized light rays substantially orthogonal to each other and a pair of right-handed circularly polarized light and left-handed circularly polarized light.

As described above, the polarizing elements 201-1 to 201-3 are disposed on substantially the same plane. Here, the polarizing element 201-1 may be shown as an example of a first polarizing element, the polarizing element 201-2 may be shown as an example of a second polarizing element, and the polarizing element 201-3 may be shown as an example of a third polarizing element. In the subsequent description, the polarizing elements 201-1, 201-2 and 201-3 respectively indicate the first polarizing element, the second polarizing element, and the third polarizing element.

Thus, the polarization filter 200 only transmits the first polarization component of the light from the living organism 190 to allow the second light receiving element 242-1 to receive the first polarization component of the light from the living organism 190, and transmits the light from the living organism 190 to allow the first light receiving elements 241 to receive the light from the living organism 190. Here, note that the second light receiving element 242-1 is one of the second light receiving elements 242. Similarly, the polarization filter 200 only transmits the second polarization component of the light from the living organism 190 to allow the second light receiving element 242-2 to receive the second polarization component of the light from the living organism 190. Here, note that the second light receiving element 242-2 is one of the second light receiving elements 242. Similarly, the polarization filter 200 only transmits the third polarization component of the light from the living organism 190 to cause the second light receiving element 242-3 to receive the third polarization component of the light from the living organism 190. Here, note that the second light receiving element 242-3 is one of the second light receiving elements 242.

The second light receiving element 242-1 may be shown as an example of a first polarized light receiving element, the second light receiving element 242-2 may be shown as an example of a second polarized light receiving element, and the second light receiving element 242-3 may be shown as an example of a third polarized light receiving element. In the following description, a plurality of second light receiving elements 242 that receive substantially the same polarization component of the light as the second light receiving element 242-1 are collectively referred to as second light receiving elements 242-1. Similarly, a plurality of second light receiving elements 242 that receive substantially the same polarization component of the light as the second light receiving element 242-2 are collectively referred to as second light receiving elements 242-2. Similarly, a plurality of second light receiving elements 242 that receive substantially the same polarization component of the light as the second light receiving element 242-3 are collectively referred to as second light receiving elements 242-3.

When the light receiving section 240 receives optical feedback from the living organism 190 in response to the light sent to the living organism 190 from the light sending section 120, the polarization filter 200 causes the second light receiving elements 242-1 to receive the first polarization component of the optical feedback from the living organism 190 in response to the light sent from the light sending section 120, causes the second light receiving elements 242-2 to receive the second polarization component of the optical feedback, and causes the third light receiving elements 242-3 to receive the third polarization component of the optical feedback.

Specifically speaking, the polarizing element 201-1 only transmits the first polarization component of the optical feedback and causes each second light receiving element 242-1 to receive the first polarization component of the optical feedback. The polarizing element 201-2 only transmits the second polarization component of the optical feedback and causes each second light receiving element 242-2 to receive the second polarization component of the optical feedback. The polarizing element 201-3 only transmits the third polarization component of the optical feedback and causes each second light receiving element 242-3 to receive the third polarization component of the optical feedback. In this manner, the polarizing elements 201-1 and 201-2 are disposed on substantially the same plane, and positioned differently from the plane on which the first and second light receiving elements 241 and 242 are arranged.

The polarization filter 200 includes light transmitting portions 310. No polarizing elements are provided in the light transmitting portions 310. Therefore, the light transmitting portions 310 transmit substantially all polarization components of the light.

Figure 4:
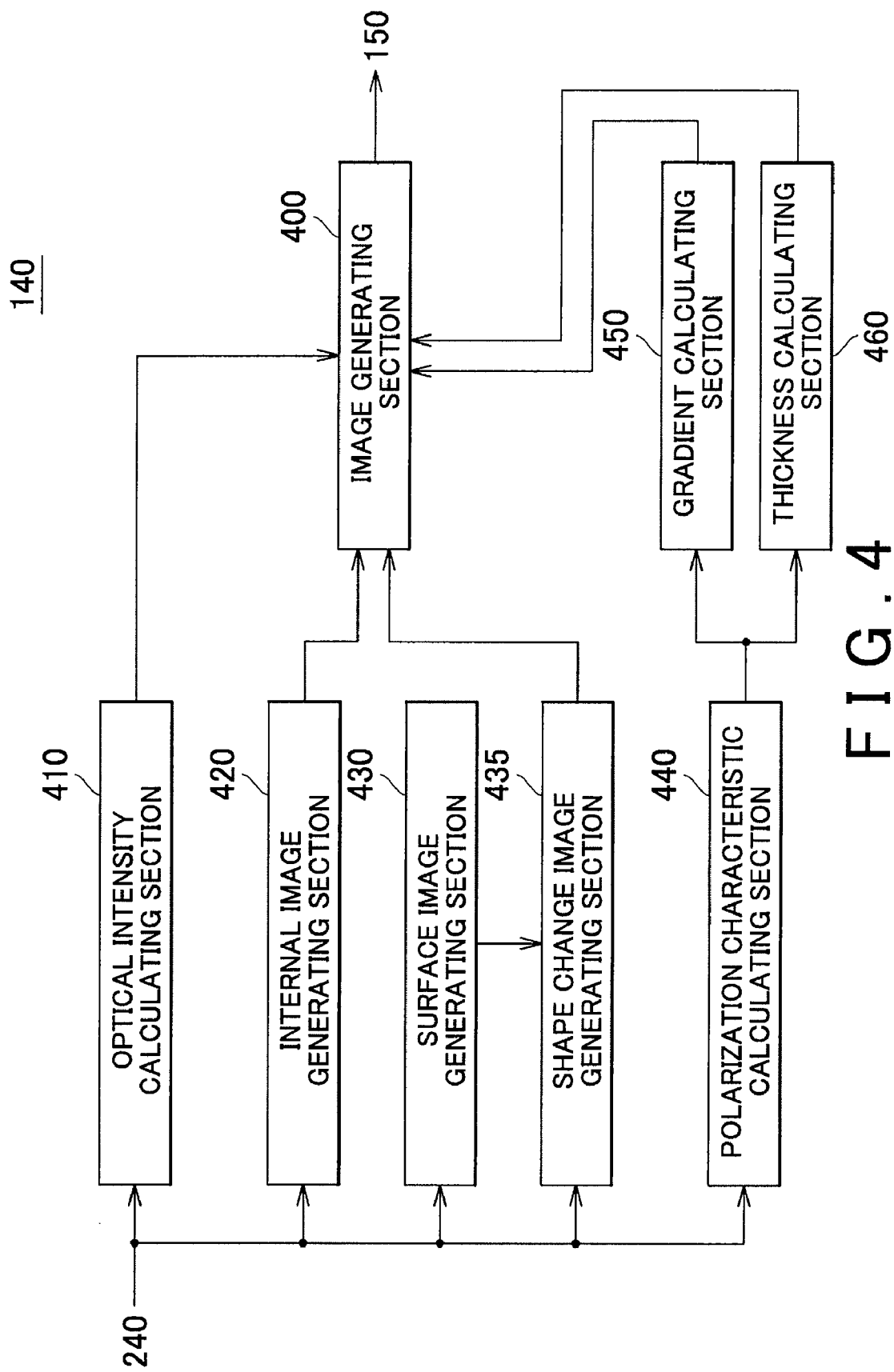
FIG. 4 illustrates an exemplary block configuration of an image processing section 140.

FIG. 4 illustrates an exemplary block configuration of the image processing section 140. The image processing section 140 includes an optical intensity calculating section 410, an internal image generating section 420, a surface image generating section 430, an image generating section 400, a shape change image generating section 435, a polarization characteristic calculating section 440, a gradient calculating section 450, and a thickness calculating section 460.

The internal image generating section 420 generates an image showing the inside of the living organism 190 by using the light received by the light receiving section 240. The surface image generating section 430 generates an image showing the surface of the living organism 190 by using the light received by the light receiving section 240.

For example, when the light sending section 120 sends, as light polarized in a specified direction, light polarized in a direction parallel to one of the transmission axes of the polarizing elements 201-1, 201-2 and 201-3, the light receiving section 240 can receive the light polarized in the specified direction and light polarized in a different direction from the specified direction in the optical feedback from the living organism 190 in response to the light sent from the light sending section 120. For example, the surface image generating section 430 generates a surface image by using the light polarized in the specified direction and the light polarized in a direction substantially orthogonal to the specified direction, both of which are received by the light receiving section 240.

As described above, when the light sending section 120 irradiates the living organism 190 with light of a specified polarization component, for example, the light polarized in the specified direction, the light receiving section 240 receives the light of the specified polarization component and light of a polarization component substantially orthogonal to the specified polarization component in the optical feedback. Specifically speaking, the light receiving section 240 receives the light polarized in the specified direction and the light polarized in the direction substantially orthogonal to the specified direction in the optical feedback.

The surface image generating section 430 generates a surface image by using the light of the specified polarization component and the light of the polarization component substantially orthogonal to the specified polarization component, both of which are received by the light receiving section 240. Specifically speaking, the surface image generating section 430 generates a surface image by using the light polarized in the specified direction and the light polarized in the direction substantially orthogonal to the specified direction, both of which are received by the light receiving section 240. The shape change image generating section 435 generates a shape change image showing a change in the shape of the surface of the living organism 190, by using a spatial change component in the surface image. Specifically speaking, the shape change image generating section 435 generates a shape change image by spatially differentiating the surface image.

As described above, the surface image generating section 430 generates the surface image showing the surface of the living organism 190, by using the light of the specified polarization component and the light of the polarization component different from the specified polarization component, both of which are received by the light receiving section 240. The shape change image generating section 435 generates the shape change image based on the surface image. Thus, the shape change image generating section 435 generates the shape change image by using the light of the specified polarization component (for example, the light polarized in the specified direction) received by the light receiving section 240.

The image generating section 400 generates a combination image by overlaying the shape change image onto the internal image, which shows the inside of the surface of the living organism 190 and is generated by using the light of the polarization component different from the specified polarization component (for example, the light polarized in the direction different from the specified direction) received by the light receiving section 240. Specifically speaking, the image generating section 400 generates the combination image by overlaying the shape change image onto the internal image generated by the internal image generating section 420 by using the light of the polarization component substantially orthogonal to the specified polarization component received by the light receiving section 240. The combination image generated by the image generating section 400 is supplied to the output section 150, to be displayed or recorded on the output section 150.

As stated above, the image generating section 400 overlays the spatial differential component of the surface image onto the internal image, there by preventing a specular reflection component from being excessively enhanced. As a result, the optical system 10 relating to the present embodiment can provide an endoscope image appropriately showing the unevenness of the surface of the living organism 190. Note that the image generating section 400 may enhance the luminance component of the internal image according to the spatial differential component of the surface image.

As described above with reference to FIG. 3, the polarizing element 201-1 only transmits the specified polarization component of the optical feedback from the living organism 190 and causes the second light receiving elements 242-1 in the light receiving section 240 to receive the specified polarization component of the optical feedback. Also, the polarizing element 201-2 only transmits the polarization component substantially orthogonal to the specified polarization component of the optical feedback and causes the second light receiving elements 242-2 in the light receiving section 240 to receive the polarization component substantially orthogonal to the specified polarization component of the optical feedback.

Accordingly, the polarization filter 200 only transmits the specified polarization component of the optical feedback from the living organism 190 and causes the second light receiving elements 242-1 in the light receiving section 240 to receive the specified polarization component of the optical feedback, and only transmits the polarization component substantially orthogonal to the specified polarization component of the optical feedback and causes the second light receiving elements 242-2 in the light receiving section 240 to receive the polarization component substantially orthogonal to the specified polarization component of the optical feedback. The surface image generating section 430 can generate the surface image by using the specified polarization component received by the first light receiving elements 241 and the polarization component substantially orthogonal to the specified polarization component received by the second light receiving elements 242.

The polarization characteristic calculating section 440 calculates the polarization characteristic of the light from the living organism 190, based on the light received by the light receiving section 240. For example, the polarization characteristic calculating section 440 calculates the polarization orientation of the light from the living organism 190 based on the light received by the light receiving section 240. Specifically speaking, the light sending section 120 irradiates the living organism 190 with circularly polarized light containing the second color component. Then, the polarization characteristic calculating section 440 calculates the polarization orientation of the light from the living organism 190, by referring to the amount of the first polarization component received by the second light receiving elements 242-1, the amount of the second polarization component received by the second light receiving elements 242-2, and the amount of the third polarization component received by the second light receiving elements 242-3.

In this manner, when the optical feedback from the living organism 190 is elliptically polarized light, the polarization characteristic calculating section 440 can calculate the polarization orientation of the elliptically polarized light based on the optical intensities of the polarization components in three different directions received by the second light receiving elements 242. The gradient calculating section 450 calculates the gradient of the surface of the living organism 190 based on the polarization orientation calculated by the polarization characteristic calculating section 440.

As described above, the polarization characteristic calculating section 440 calculates the polarization characteristic of the light from the living organism 190, by referring to the amount of the first polarization component received by the second light receiving elements 242-1, the amount of the second polarization component received by the second light receiving elements 242-2, and the amount of the third polarization component received by the second light receiving elements 242-3. Examples of the polarization characteristic may include a degree of polarization, in addition to the above-mentioned polarization orientation.

As described with reference to FIG. 3, the polarization filter 200 allows the second light receiving elements 242-1 to receive the first polarization component of the light from the living organism 190, allows the second light receiving elements 242-2 to receive the second polarization component of the light from the living organism 190, and allows the second light receiving elements 242-3 to receive the third polarization component of the light from the living organism 190. The polarization characteristic calculating section 440 can calculate the spatial distribution of the polarization characteristic of the light from the living organism 190, based on the amount of the first polarization component received by the second light receiving elements 242-1, the amount of the second polarization component light received by the second light receiving elements 242-2, and the amount of the third polarization component received by the second light receiving elements 242-3. Thus, the polarization characteristic calculating section 440 can calculate the distribution of the gradient of the surface of the living organism 190 or the distribution of the degree of polarization.

The optical intensity calculating section 410 calculates the optical intensity of the second color component of the light from the living organism 190, based on the amount of the first polarization component received by the second light receiving elements 242-1 and the amount of the second polarization component received by the second light receiving elements 242-2. The image generating section 400 then generates an image of the living organism 190 based on the optical intensity calculated by the optical intensity calculating section 410, and the amount of the light received by the first light receiving elements 241. According to the optical system 10 relating to the present embodiment, the second light receiving elements 242, which are configured to receive blue light, each receive a different polarization component of light, but the optical intensity calculating section 410 can calculate the optical intensity of the blue light. Therefore, the optical system 10 relating to the present embodiment can generate an appropriate visible light image. With such a configuration, more polarizing elements 201 can be associated with the second light receiving elements 242. As a result, the optical system 10 can provide polarization information in higher resolution.

Also, the optical system 10 can calculate the thickness of a scattering medium. For example, the living organism 190 often scatters light. If such a scattering layer has there under a lower medium that feeds back polarized light, the polarization characteristic of the optical feedback is expected to vary in accordance with the change in the thickness of the scattering layer. Therefore, the thickness calculating section 460 calculates the thickness of the scattering layer according to the degree of polarization of the optical feedback from the living organism 190.

Specifically speaking, the light sending section 120 sends light to the living organism 190 that has a scattering medium scattering light and a lower medium positioned under the scattering medium. The lower medium feeds back polarized light in response to light incident thereon towards the source of the incident light. The light receiving section 240 then receives the light that is sent from the light sending section 120 and then scattered by the scattering medium, as well as the light from the lower medium. The thickness calculating section 460 calculates the thickness of the scattering medium to the lower medium, based on at least one of the non-polarization component and the polarization component of the light received by the light receiving section 240. Herein, the term "lower" indicates the lower side of the scattering medium not only in the gravitational direction but also with respect to the light sending section 120.

During the initial stage of a cancer in a mucosa of a stomach, for example, the thickness of the mucosal layer varies according to the type, progression stage and other parameters of the cancer. In light of this, the optical system 10 may be capable of easily identifying the location of the cancer or the like, through the thickness detection of the mucosa with the use of the thickness calculating section 460.

FIG. 5 illustrates an exemplary image 500 produced by the endoscope 100. The image 500 may be an example of the image obtained by exposing the light receiving section 240 of the image capturing section 110 to light with the polarization filter 126 being positioned outside the optical path. The image 500 has a blood vessel image 510 and a specular reflection image 520. The blood vessel image 510 shows inside the surface of the living organism 190, which is imaged by the endoscope 100, and the specular reflection image 520 is formed by light that is sent from the light sending section 120 and then specularly reflected by the surface of the living organism 190.

The image 500 roughly provides the unevenness information about the surface of the living organism 190. However, since the image 500 has the specular reflection image 520, the information about the living organism 190 cannot be visually observed in the region of the specular reflection image 520. For example, a pigment change component and detailed unevenness information about the surface cannot be visually observed.

Figure 6:
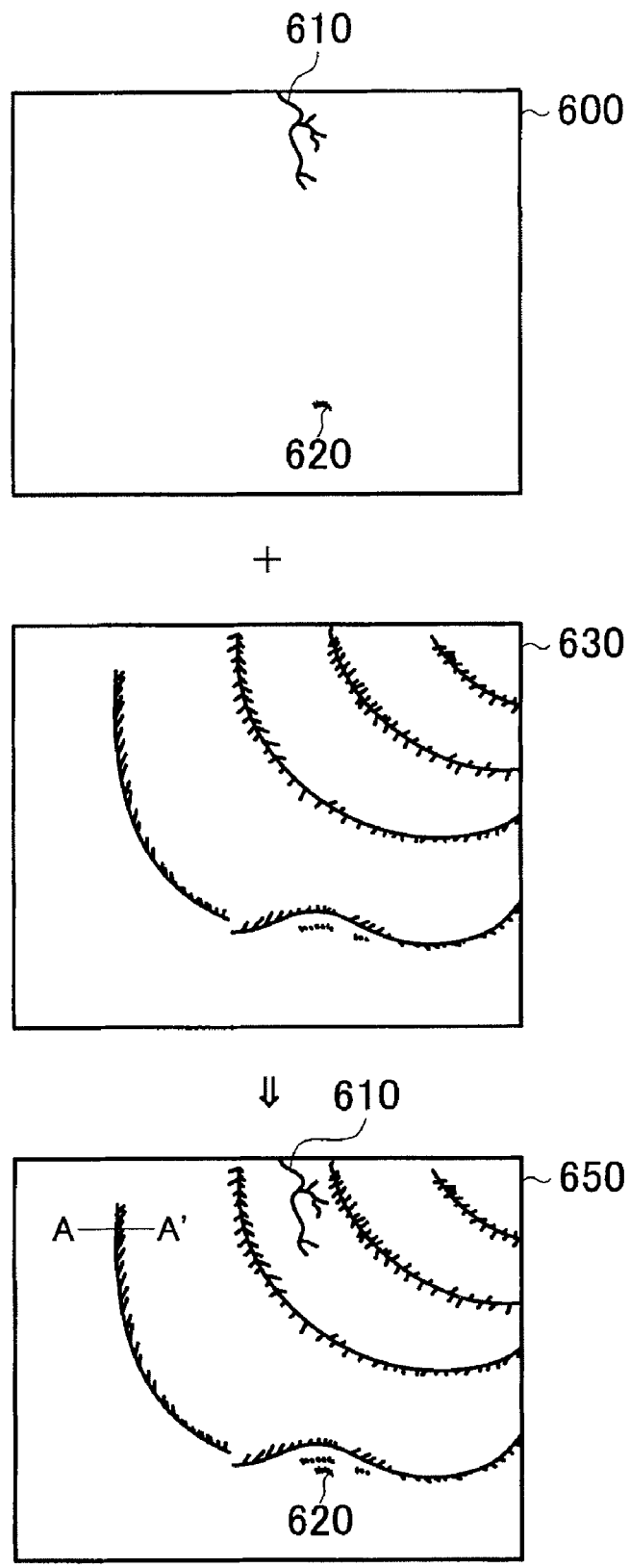
FIG. 6 illustrates an exemplary internal image 600, an exemplary shape change image 630, and an exemplary combination image 650.

FIG. 6 illustrates an exemplary internal image 600, an exemplary shape change image 630, and an exemplary combination image 650. The internal image generating section 420 generates the internal image 600 by using light, received by the light receiving section 240, that is polarized in a direction orthogonal to the polarization direction of the light sent from the light sending section 120. The internal image 600 shows the inside of the living organism 190, and has a blood vessel image 610 and a pigment change component 620.

The shape change image generating section 435 calculates the shape change image 630 by spatially differentiating the surface image. The spatial differentiation can enhance the spatial luminance change component and attenuate the signal intensity of a high luminance region such as specular reflection light. Thus, the shape change image generating section 435 can produce the shape change image 630 appropriately showing the surface unevenness information. The image generating section 400 generates the combination image 650 by overlapping together the internal image 600 and the shape change image 630 with predetermined weights. In the combination image 650, the pigment change component 620 can be visually observed, which is hidden by the specular reflection image 520 in the image 500. Also, the unevenness is enhanced in the combination image 650, and the pigment change component 620 can be thus found to be present on a convex portion of the surface of the living organism 190.

As described above, the optical system 10 can incorporate the surface unevenness information into the internal image 600. Therefore, an observer can visually observe the inside of the living organism 190, in association with the surface unevenness information of the living organism 190. In other words, the optical system 10 can provide the observer with an easy-to-visually-observe image. Also, the optical system 10 superposes the shape change image 630, which is equivalent to the spatial differential component of the surface image, onto the internal image 600. Therefore, the optical system 10 can enhance the unevenness of the surface while reducing the glare caused by the specular reflection light. The image generating section 400 may perform conversion on the shape change image 630 and the internal image 600 with different LUTs and combine together the resulting images.

Figure 7:
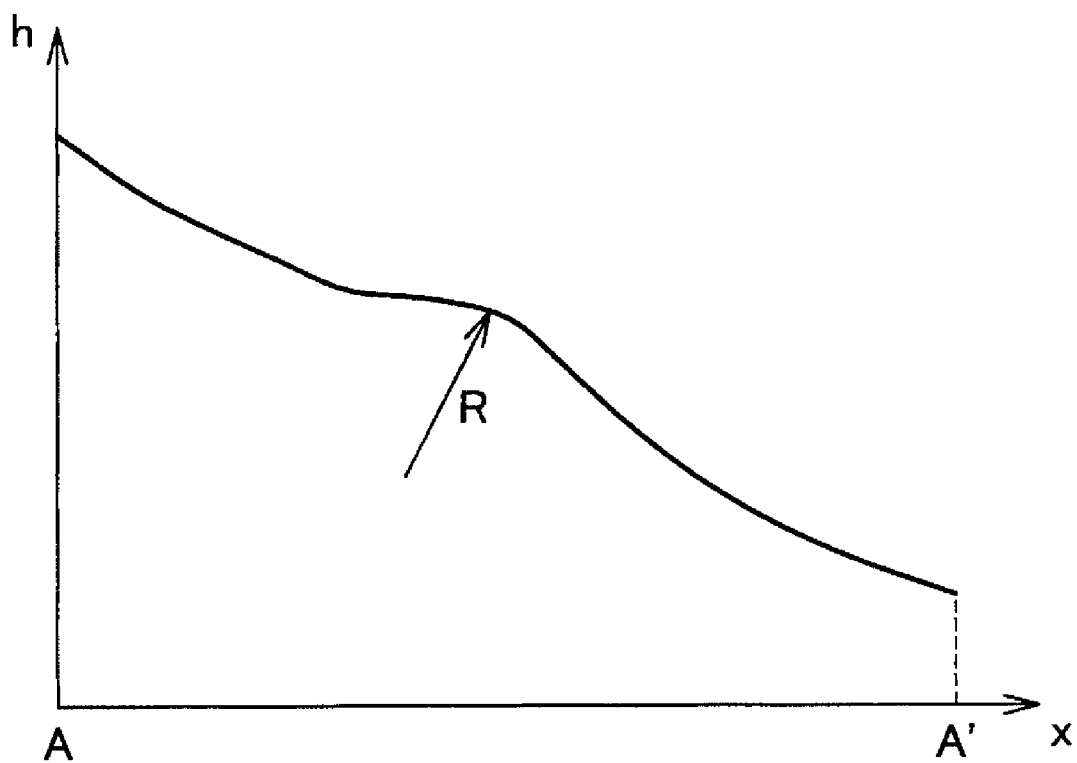
FIG. 7 illustrates an example of a gradient.

FIG. 7 illustrates an exemplary method used by the gradient calculating section 450 to calculate a gradient. As described above, the gradient calculating section 450 calculates the angle of the gradient, by referring to the polarization orientation calculated by the polarization characteristic calculating section 440. Here, the gradient calculating section 450 may prestore surface gradient information of the living organism 190 in association with the polarization orientation of elliptically polarized light. The gradient calculating section 450 then extracts surface gradient information stored in association with the polarization orientation calculated by the polarization characteristic calculating section 440. The surface gradient information can be exemplified by the curvature R of the surface.

The gradient information calculated by the gradient calculating section 450 may be supplied to the image generating section 400. Since the polarization characteristic calculating section 440 can calculate a two-dimensional distribution of the polarization characteristic as has been described earlier, the gradient calculating section 450 can calculate a two-dimensional distribution of the gradient information. Therefore, the image generating section 400 can generate an image representing the two-dimensional distribution of the gradient based on the gradient information calculated by the gradient calculating section 450.

Figure 8:
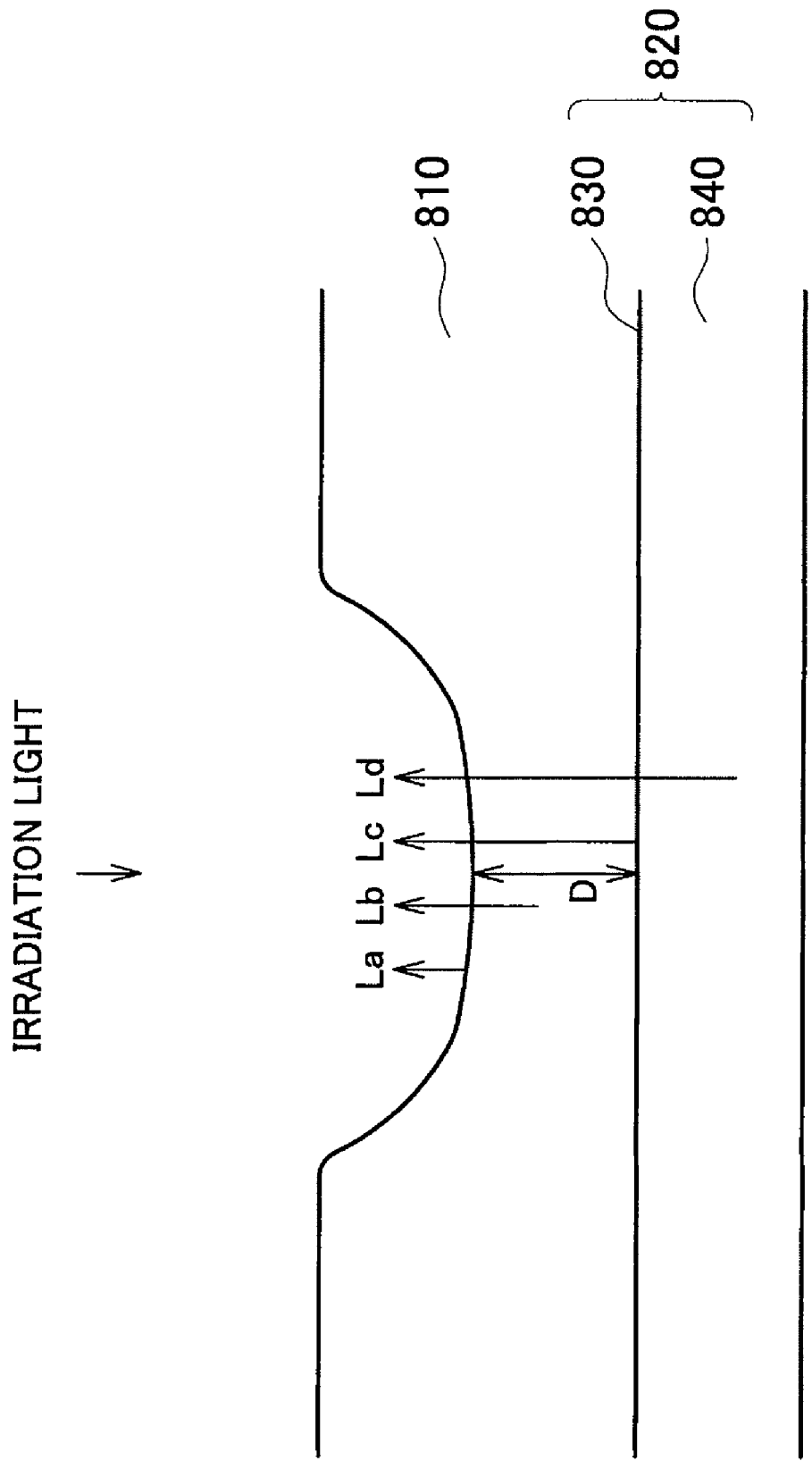
FIG. 8 schematically illustrates the structure of a stomach wall, which is shown as an example of the living organism 190.

FIG. 8 schematically illustrates the structure of a stomach wall, which is shown as an example of the living organism 190. The stomach wall has a mucosa 810, a muscular is mucosae 830 and a submucosa 840 formed in the stated order from the surface of the living organism 190 downwards. When the light sending section 120 irradiates the living organism 190 with light, the light receiving section 240 receives, as optical feedback, light La that is reflected by the front surface of the mucosa 810, light Lb that is scattered within the mucosa 810, which is shown as an example of a scattering medium, light Lc that is reflected by the front surface of the muscularis mucosae 830, which is shown as an example of a reflection medium, and light Ld that comes from within the submucosa 840 with polarization anisotropy.

The muscularis mucosae 830 and the submucosa 840 feedback polarized light in response to the irradiation light incident thereon, as described later. Therefore, the muscularis mucosae 830 and the submucosa 840 can be considered as the lower medium 820 that feeds back polarized light in response to light incident thereon.

When the light sending section 120 irradiates the living organism 190 with polarized light, the surface reflected light La is polarized. Also, the light LC that is reflected by the muscularis mucosae 830, which is configured as a reflection medium, is polarized. Furthermore, the optical feedback Ld from the submucosa 840 containing collagen with polarization anisotropy can include a polarized component. On the other hand, the light Lb that is sent from the light sending section 120 and then scattered by the mucosa 810, configured as a scattering medium, is substantially non-polarized. Therefore, as the thickness D of the mucosa 810 increases, the optical feedback from the living organism 190 is expected to become more non-polarized.

When the light sending section 120 irradiates the living organism 190 with non-polarized light, the surface reflected light La, the scattered light Lb from the inside of the mucosa 810, and the light Lc reflected by the muscularis mucosae 830 are substantially non-polarized, but the light Ld may include a polarized component. Therefore, when the light sending section 120 irradiates the living organism 190 with non-polarized light, the optical feedback from the living organism 190 is also expected to become more non-polarized in accordance with the increase in the thickness D of the mucosa 810. Considering the above, the thickness calculating section 460 calculates the thickness of the scattering medium based on the degree of polarization of the optical feedback received by the light receiving section 240. Specifically speaking, as the degree of polarization of the light received by the light receiving section 240 decreases, the thickness calculating section 460 increases the thickness of the scattering medium (for example, the mucosa 810) to be calculated.

As described with reference to FIG. 3, the polarization filter 200 selectively transmits different polarization components of the light from the living organism 190 and causes a plurality of light receiving elements (for example, the second light receiving elements 242) in the light receiving section 240 to receive the different polarization components. The polarization characteristic calculating section 440 can calculate the degree of polarization based on the light reception amounts of the plurality of light receiving elements such as the second light receiving elements 242. The thickness calculating section 460 increases the thickness of the scattering medium to be calculated, as the degree of polarization calculated by the polarization characteristic calculating section 440 decreases.

The light sending section 120 may irradiate the living organism 190 with light of a specified polarization component. In this case, the light received by the light receiving section 240 has the same specified polarization component as the light sent from the light sending section 120. The thickness calculating section 460 may increase the thickness of the scattering medium to be calculated, as the intensity of the specified polarization component of the light received by the light receiving section 240 decreases.

As described above, whether the light sending section 120 irradiates the living organism 190 with polarized light or non-polarized light, the thickness calculating section 460 increases the thickness of the scattering medium to be calculated as the degree of polarization of the light received by the light receiving section 240 decreases. In this manner, the optical system 10 can detect a spatial change in the thickness of the mucosa 810. As a consequence, the optical system 10 may be capable of detecting a decrease in the thickness D of the mucosa 810 that is caused by progression of a cancer.

FIG. 9 illustrates exemplary thickness information stored on the thickness calculating section 460 by using a table. The thickness calculating section 460 prestores the thickness of the scattering medium in association with the degree of polarization. The thickness calculating section 460 supplies, as the thickness of the scattering medium, a thickness stored in association with the degree of polarization of the light received by the light receiving section 240.

The thickness information calculated by the thickness calculating section 460 may be supplied to the image generating section 400. Since the polarization characteristic calculating section 440 can calculate a two-dimensional distribution of the degree of polarization as described above, the thickness calculating section 460 can calculate a two-dimensional distribution of the thickness. Therefore, the image generating section 400 may generate an image showing the thickness of the scattering layer, by using the thickness information supplied by the thickness calculating section 460. For example, the image generating section 400 may generate an image by modulating, with the thickness information of the scattering layer, the luminance information of an image of the living organism 190 produced by the endoscope 100. With the above-described configuration, the optical system 10 can easily display an image showing the thickness of the scattering layer.

Figure 10:
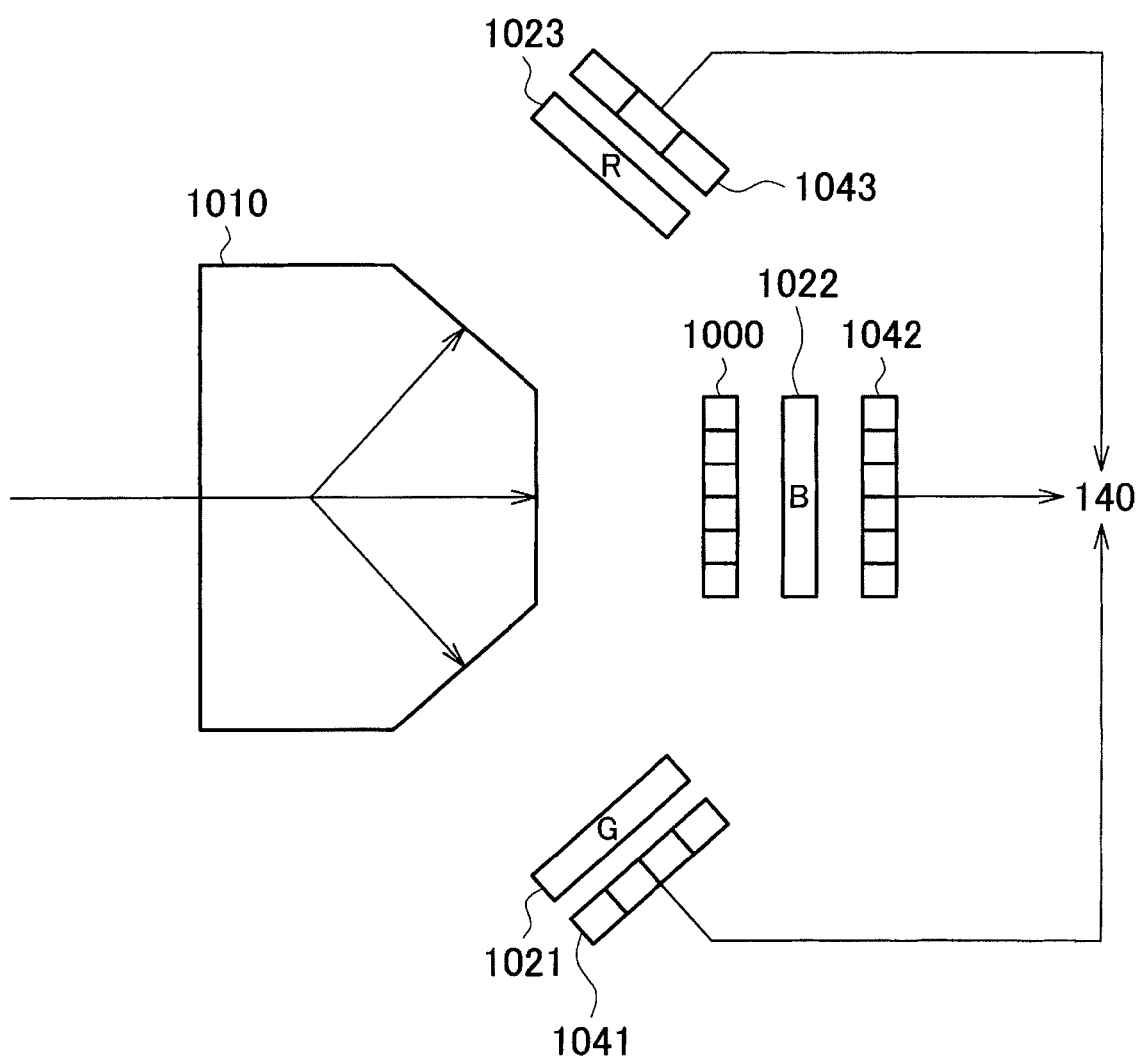
FIG. 10 illustrates another exemplary configuration of the image capturing section 110.

FIG. 10 illustrates another exemplary configuration of the image capturing section 110. According to the present exemplary configuration, the image capturing section 110 has a so-called 3CCD structure.

The image capturing section 110 includes an optical system 1010 that separates optical feedback into different components, a color filter 1021 that transmits green light, a color filter 1022 that transmits blue light, a color filter 1023 that transmits red light, a light receiving element array 1041 that receives green light, a light receiving element array 1042 that receives blue light, a light receiving element array 1043 that receives red light, and a polarization filter 1000. The optical system 1010 includes a lens 112, and separates the optical feedback from the living organism 190 into components to be supplied to the light receiving element arrays 1041, 1042 and 1043.

The light receiving element array 1041 receives green light, which is produced by the optical system 1010 and has been transmitted through the color filter 1021. The light receiving element array 1043 receives red light, which is produced by the optical system 1010 and has been transmitted through the color filter 1023. The light receiving element array 1042 receives blue light, which is produced by the optical system 1010 and has been transmitted through the polarization filter 1000 and the color filter 1022.

The light receiving element arrays 1041, 1042 and 1043 are each formed in such a manner that a plurality of light receiving elements are arranged on substantially the same plane. As schematically illustrated in FIG. 10, the light receiving elements are arranged with the highest area density in the light receiving element array 1042, from among the light receiving element arrays 1041, 1042 and 1043. The polarization filter 1000 is formed in such a manner that polarizing elements that transmit light rays of different polarization characteristics are arranged in a matrix on the same plane, similarly to the polarization filter 200. The image capturing section 110 employing a multi-CCD structure, such as shown in FIG. 10, can also measure polarization information with a high resolution, by configuring a light receiving element array having a higher area density to receive light polarized in different directions.

According to the above embodiment, blue light receiving elements are arranged with the highest area density for the purpose of observing living organisms. According to a different embodiment, however, green light receiving elements may be arranged with the highest area density. In this case, the green light receiving elements may be controlled to receive light polarized in different directions.

According to the above embodiment, the light receiving element array having the highest density is controlled to receive light polarized in different directions. Here, transmission of light through the polarization filter 200 lowers the optical intensity of the light. In light of this, a different embodiment may be configured in such a manner that a light receiving element array expected to receive light of a certain color having the highest optical intensity receives light polarized in different directions.

Thus, in the light receiving section 240, the second light receiving elements 242 may be configured to receive, from the living organism 190, the second-color component light having a higher optical intensity than the first-color component light. For example, the second light receiving elements 242 may be configured to receive the red component of the light from the living organism 190, and the first and third light receiving elements 241 and 243 may be configured to receive other color components of the light from the living organism 190. For example, the first light receiving elements 241 may be configured to receive the green or blue component of the light. Here, the color components of light may be exemplified by color components defined in the complementary color system, in addition to R, G and B components defined in the primary color system.

When the first and second light receiving elements 241 and 242 receive light that is sent from the light sending section 120 and reflected by the living organism 190, the reflectance of the living organism 190 may be higher in the wavelength range of the light to be received by the second light receiving elements 242 than in the wavelength range of the light to be received by the first light receiving elements 241. Furthermore, the value obtained by multiplying the reflectance in the wavelength range of the light to be received by the second light receiving elements 242 by the light reception sensitivity of the second light receiving elements 242 may be higher than the value obtained by multiplying the reflectance in the wavelength range of the light to be received by the first light receiving elements 241 by the light reception sensitivity of the first light receiving elements 241. In addition, a larger light receiving area may be achieved by the second light receiving elements 242 than by the first light receiving elements 241.

Figure 11:
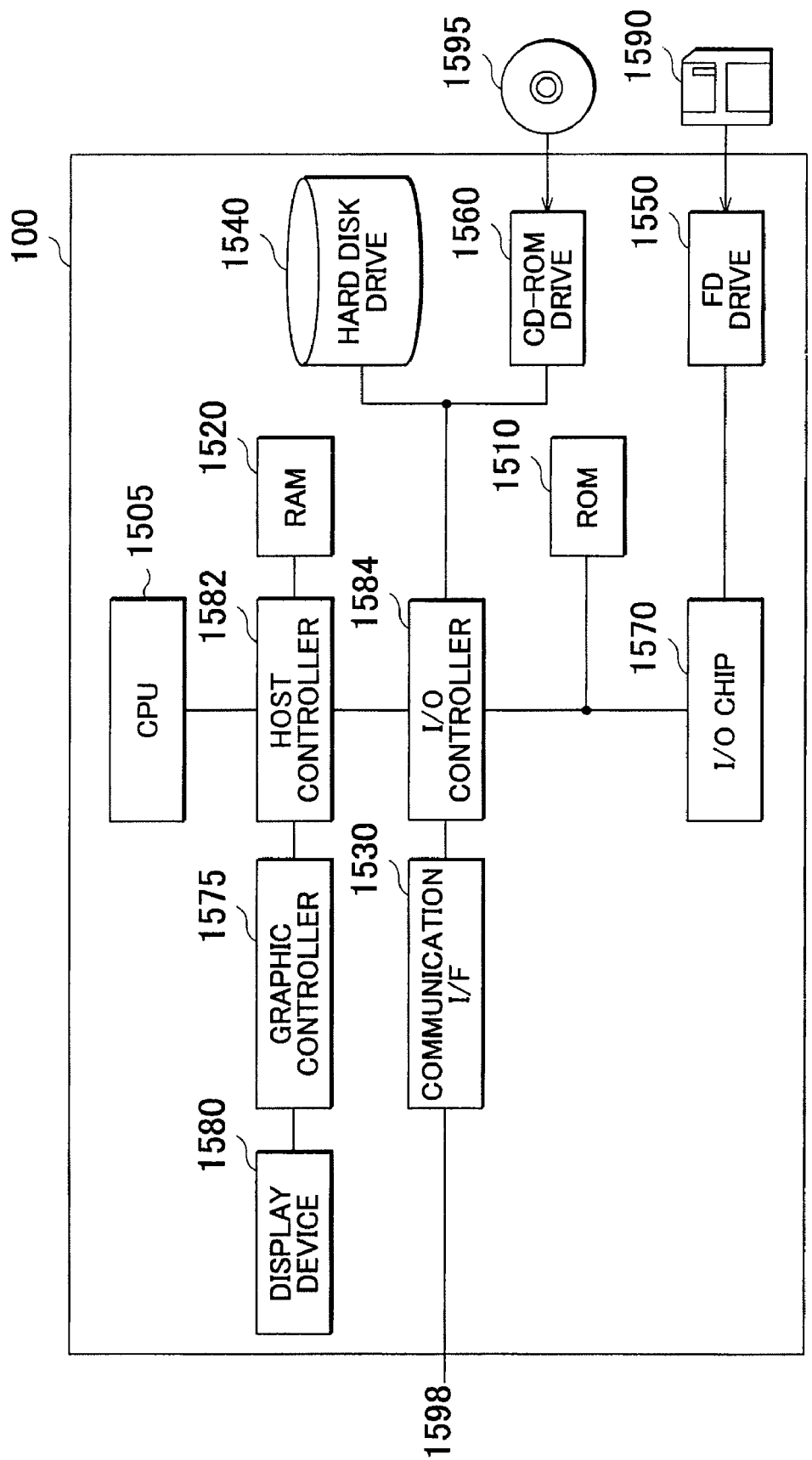
FIG. 11 illustrates an exemplary hardware configuration of the optical system 10.

FIG. 11 illustrates an exemplary hardware configuration of the optical system 10. The optical system 10 is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The hard disk drive 1540 stores thereon programs and data to be used by the CPU 1505. The communication interface 1530 couples to the network communication apparatus 1598, to transmit/receive programs or data. The CD-ROM drive 1560 reads programs or data from a CD-ROM 1595, and supplies the read programs or data to the hard disk drive 1540 and communication interface 1530 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the optical system 10 at the start up, programs dependent on the hardware of the optical system 10 and the like. The flexible disk drive 1550 reads programs or data from a flexible disk 1590, and supplies the read programs or data to the hard disk drive 1540 and communication interface 1530 via the RAM 1520. The I/O chip 1570 is used to connect a variety of I/O devices such as the flexible disk drive 1550 via, for example, a parallel port, a serial port, a keyboard port, a mouse port or the like.

The program to be executed by the CPU 1505 is provided by a user in the state of being stored on a recording medium such as the flexible disk 1590, the CD-ROM 1595, and an IC card. The program may be stored on the recording medium in the state of being compressed or not being compressed. The program is installed from the recording medium onto the hard disk drive 1540, read by the RAM 1520, and executed by the CPU 1505. The program executed by the CPU 1505 causes the optical system 10 to function as the respective constituents of the optical system 10 described with reference to FIGS. 1 to 10.

The program mentioned above may be stored on an external recording medium. The recording medium is, for example, an optical recording medium such as DVD and PD, a magnet-optical recording medium such as MD, a tape medium, a semiconductor memory such as an IC card and the like, in addition to the flexible disk 1590 and CD-ROM 1595. The recording medium may be a storage device such as a hard disk or RAM which is provided in a server system connected to a dedicated communication network or the Internet, and the program may be provided to the optical system 10 via the network. In this way, a computer is controlled by the program to function as the optical system 10.

Although some aspects of the present invention have been described by way of exemplary embodiments, it should be understood that those skilled in the art might make many changes and substitutions without departing from the spirit and the scope of the present invention which is defined only by the appended claims.

The claims, specification and drawings describe the processes of an apparatus, a system, a program and a method by using the terms such as operations, procedures, steps and stages. When a reference is made to the execution order of the processes, wording such as "before" or "prior to" is not explicitly used. The processes may be performed in any order unless an output of a particular process is used by the following process. In the claims, specification and drawings, a flow of operations may be explained by using the terms such as "first" and "next" for the sake of convenience. This, however, does not necessarily indicate that the operations should be performed in the explained order.

What is claimed is:

1. An optical system comprising:
    a light sending section that sends light to an object having a scattering medium and a lower medium positioned below the scattering medium, the scattering medium scattering light, the lower medium feeding back polarized light in response to light incident thereon;
    a light receiving section that receives (i) light that is sent from the light sending section and then scattered by the scattering medium and (ii) light from the lower medium; and
    a thickness calculating section that calculates a thickness of the scattering medium, by referring to at least one of a non-polarization component and a polarization component of the light received by the light receiving section; wherein
    the thickness calculating section determines that the thickness of the scattering medium increases as the degree of polarization of the light received by the light receiving section decreases.

2. The optical system as set forth in claim 1, wherein
    the thickness calculating section calculates the thickness of the scattering medium by referring to a degree of polarization of the light received by the light receiving section.

3. The optical system as set forth in claim 1, wherein
    the light sending section sends polarized light to the object, and
    the thickness calculating section determines that the thickness of the scattering medium increases as the degree of polarization of the light received by the light receiving section decreases.

4. The optical system as set forth in claim 3, wherein
    the light sending section sends the polarized light to the object having the scattering medium and the lower medium that is a reflective medium reflecting the polarized light incident thereon, and
    the light receiving section receives (i) the light that is sent from the light sending section and then scattered by the scattering medium and (ii) light that is sent from the light sending section and then reflected by a surface of the lower medium.

5. The optical system as set forth in claim 3, further comprising:
    a polarizing section that transmits a plurality of different polarization components of light from the object to cause a plurality of light receiving elements in the light receiving section respectively to receive the plurality of different polarization components; and
    a polarization characteristic calculating section that calculates the degree of polarization by referring to an amount of light received by each of the plurality of light receiving elements, wherein
    the thickness calculating section determines that the thickness of the scattering medium increases as the degree of polarization of the light received by the light receiving section decreases.

6. The optical system as set forth in claim 5, wherein
    the polarizing section includes a plurality of polarizing elements that transmit the plurality of different polarization components of the light from the object and causes the plurality of light receiving elements respectively to receive the plurality of different polarization components, and
    the plurality of polarizing elements are arranged on substantially the same plane.

7. The optical system as set forth in claim 1, wherein
    the light sending section sends non-polarized light to the object, and the thickness calculating section determines that the thickness of the scattering medium increases as the degree of polarization of the light received by the light receiving section decreases.

8. The optical system as set forth in claim 7, wherein
the light sending section sends the non-polarized light to the object having the scattering medium and the lower medium that has polarization anisotropy, and
the light receiving section receives (i) the light that is sent from the light sending section and then scattered by the scattering medium and (ii) optical feedback from the lower medium.

9. The optical system as set forth in claim 1, wherein
the light sending section sends light with a specified polarization component to the object having the scattering medium and the lower medium that is a reflective medium reflecting the light incident thereon,
the light receiving section receives (i) the light that is sent from the light sending section and then scattered by the scattering medium and (ii) light that is sent from the light sending section and then reflected by the lower medium, and
the thickness calculating section determines that the thickness of the scattering medium increases as the degree of polarization of the light received by the light receiving section decreases.

10. The optical system as set forth in claim 1, wherein
the light sending section sends non-polarized light to the object, and
the thickness calculating section determines that the thickness of the scattering medium increases as the degree of polarization of the light received by the light receiving section decreases.

11. The optical system as set forth in claim 1, wherein
the thickness calculating section prestores the thickness of the scattering medium in association with the degree of polarization; and wherein
the thickness calculating section supplies, as the thickness of the scattering medium, a thickness stored in association with the degree of polarization of the light received by the light receiving section.

12. The optical system as set forth in claim 1, wherein
the scattering medium is a mucosa, and the lower medium is a muscularis mucosae and a submucosa.

13. A method comprising:
sending light to an object having a scattering medium and a lower medium positioned below the scattering medium, the scattering medium scattering light, the lower medium feeding back polarized light in response to light incident thereon;
receiving (i) light that is sent in the light sending and then scattered by the scattering medium and (ii) light from the lower medium; and
calculating a thickness of the scattering medium, by referring to at least one of a non-polarization component and a polarization component of the light received in the light receiving; wherein
calculating the thickness comprises increasing the thickness of the scattering medium to be calculated, as the degree of polarization of the light received decreases.

14. A method as set forth in claim 13, wherein
the thickness calculating includes prestoring the thickness of the scattering medium in association with the degree of polarization; and
supplying, as the thickness of the scattering medium, a thickness stored in association with the degree of polarization of the light received by the light receiving step.

15. A method as set forth in claim 13, wherein
the scattering medium is a mucosa, and the lower medium is a muscularis mucosae and a submucosa.

16. A non-transitory computer readable medium storing thereon a program for use with an optical system, the program causing a computer to function as:
a light sending section that sends light to an object having a scattering medium and a lower medium positioned below the scattering medium, the scattering medium scattering light, the lower medium feeding back polarized light in response to light incident thereon;
a light receiving section that receives (i) light that is sent from the light sending section and then scattered by the scattering medium and (ii) light from the lower medium; and
a thickness calculating section that calculates a thickness of the scattering medium, by referring to at least one of a non-polarization component and a polarization component of the light received by the light receiving section; wherein
the thickness calculating section determines that the thickness of the scattering medium increases as the degree of polarization of the light received by the light receiving section decreases.

17. A non-transitory computer readable medium storing thereon a program for use with an optical system as set forth in claim 16, wherein
the thickness calculating section prestores the thickness of the scattering medium in association with the degree of polarization; and wherein
the thickness calculating section supplies, as the thickness of the scattering medium, a thickness stored in association with the degree of polarization of the light received by the light receiving section.

18. A non-transitory computer readable medium storing thereon a program for use with an optical system as set forth in claim 16, wherein
the scattering medium is a mucosa, and the lower medium is a muscularis mucosae and a submucosa.

* * * * *